United States Patent
Tudor

(10) Patent No.: US 12,097,052 B2
(45) Date of Patent: *Sep. 24, 2024

(54) HEALTH MONITOR WEARABLE DEVICE

(71) Applicant: Gaia Connect Inc., West Palm Beach, FL (US)

(72) Inventor: Adinel Tudor, Bucharest (RO)

(73) Assignee: Gaia Connect Inc., West Palm Beach, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/894,303

(22) Filed: Aug. 24, 2022

(65) Prior Publication Data
US 2022/0401040 A1 Dec. 22, 2022

Related U.S. Application Data

(63) Continuation of application No. 15/883,429, filed on Jan. 30, 2018, now Pat. No. 11,445,986.

(51) Int. Cl.
*A61B 5/00* (2006.01)
*A61B 5/0205* (2006.01)
*A61B 5/024* (2006.01)
*A61B 5/11* (2006.01)

(52) U.S. Cl.
CPC ............ *A61B 5/747* (2013.01); *A61B 5/0004* (2013.01); *A61B 5/0022* (2013.01); *A61B 5/0205* (2013.01); *A61B 5/1112* (2013.01); *A61B 5/1117* (2013.01); *A61B 5/681* (2013.01); *A61B 5/7267* (2013.01); *A61B 5/7455* (2013.01); *A61B 5/746* (2013.01); *A61B 5/02438* (2013.01); *A61B 2560/0475* (2013.01); *A61B 2562/0219* (2013.01)

(58) Field of Classification Search
None
See application file for complete search history.

(56) References Cited

U.S. PATENT DOCUMENTS

| 5,304,206 A * | 4/1994 | Baker, Jr. ............ A61N 1/37217 607/45 |
| 6,160,478 A * | 12/2000 | Jacobsen .............. A61B 5/6838 128/903 |
| 11,445,986 B2 * | 9/2022 | Tudor .................... A61B 5/747 |

(Continued)

FOREIGN PATENT DOCUMENTS

WO  WO-2014098765 A1 *  6/2014 ........... A61B 5/0022

*Primary Examiner* — Benjamin S Melhus
*Assistant Examiner* — Samuel C Kim
(74) *Attorney, Agent, or Firm* — ArentFox Schiff LLP

(57) ABSTRACT

Disclosed are systems and methods for detecting a fall of a user of a wearable device. The described system samples signal data from an accelerometer of the wearable device and performs a preliminary determination of fall detection using pattern recognition. This preliminary detection may be based on whether a first portion of the signal data exceeds a first threshold indicative of a fall of a wearer of the electronic device and whether a second portion of the signal data is within a range indicative of motion stillness following the fall. The described system further applies a machine learning classifier to the signal data associated with the preliminary indication to generate a fall classification indicating the signal data represents a fall of the wearer of the electronic device.

18 Claims, 6 Drawing Sheets

(56) References Cited

U.S. PATENT DOCUMENTS

| | | | | |
|---|---|---|---|---|
| 2005/0107838 | A1* | 5/2005 | Lovett | A61B 5/4818 |
| | | | | 607/42 |
| 2006/0279426 | A1* | 12/2006 | Bonnet | A61B 5/1117 |
| | | | | 340/573.1 |
| 2008/0272918 | A1* | 11/2008 | Ingersoll | A61B 5/0002 |
| | | | | 600/595 |
| 2009/0322540 | A1* | 12/2009 | Richardson | G08B 21/0446 |
| | | | | 340/573.7 |
| 2012/0116187 | A1* | 5/2012 | Hayes | A61B 5/6887 |
| | | | | 600/587 |
| 2014/0379255 | A1* | 12/2014 | Johnson | A61B 5/0006 |
| | | | | 701/470 |
| 2018/0220973 | A1* | 8/2018 | Asianto | A61B 5/681 |

* cited by examiner

HEALTH MONITOR WEARABLE DEVICE

CROSS-REFERENCE TO RELATED APPLICATIONS

This application is a continuation of U.S. Non-Provisional application Ser. No. 15/883,429 filed on Jan. 30, 2018, which is herein incorporated by reference.

FIELD OF TECHNOLOGY

The present disclosure relates generally to the field of monitoring well-being information using a wearable device, more specifically, to systems and methods of detecting falls or abnormal heart rates of wearers of an electronic device.

BACKGROUND

Falls among elderly people is a significant cause of injury and hospital admissions. It is important to get help to people if they fall as quickly as possible, as it has been shown that the longer the delay for receiving medical care, the higher the risk of death, a lengthy hospital stay, or admission to a nursing home. It is noted that falls are not an issue exclusive to elderly people living in their own homes. People in residing in rehabilitation hospitals, acute-care, psychiatric hospitals, nursing facilities, and independent and assisted living facilities also face similar risks.

One conventional solution for fall detection employs a manual "panic button", sometimes referred to as a personal emergency response system, e.g., Philips LifeLine®. If a person has fallen or otherwise requires help, the person may push the button on a transmitter device that is worn around the person's neck. Some models of personal emergency response systems would also detect automatically a fall. The devices are neck-worn pendants, where the transmitter sends a radio signal either to a speaker-telephone equipped with a receiver, or via cellular network. The reception of the radio signal causes the speaker-telephone to call a preprogrammed telephone number of a third-party response center, where an operator at the response center assists or dispatches help to the person.

Known solutions for fall detection have numerous drawbacks. For example, the panic-button based system requires manual activation by a person, which may be unavailable if the person is rendered seriously injured or unconscious by the fall. In another drawback, current systems typically require the use of a call-center or other third party intervention services, which are costly, and fail to contact family members or caregivers. Finally, many elderly people have reported they do not enjoy wearing a neck-hanging device. As such, the panic-button/neck-hanging based systems are rendered ineffective due to patient compliance issues (i.e., users fail to wear the device regularly or otherwise forget to keep them within arm's reach at all times).

SUMMARY

Accordingly, aspects of the present disclosure provide a wrist-worn wearable device and system that provides real-time information for family members and caregivers using seamlessly the internet connection at home of the person wearing it, together with cellular connectivity integrated into the wearable device.

In one aspect, an apparatus for detecting a fall of a wearer of the apparatus includes a wireless communication component, at least one sensor comprising an accelerometer configured to measure motion of the apparatus, and a processor. The processor is configured to sample signal data received from the accelerometer, and responsive to determining that a first portion of the signal data exceeds a first threshold indicative of a fall of a wearer of the electronic device and that a second portion of the signal data is within a range indicative of motion stillness following the fall, generate a preliminary indication of fall detection associated with the signal data. The processor is further configured to apply a machine learning classifier to the signal data associated with the preliminary indication to generate a fall classification indicating the signal data represents a fall of the wearer of the electronic device. The processor is further configured to transmit, via the wireless communication component of the electronic device, a notification that the wearer of the electronic device has fallen.

In another aspect, the first portion of the signal data includes a first channel of signal data from the accelerometer during a first time period, and the second portion of the signal data includes a second channel of signal data from the accelerometer during a second time period subsequent to the first time period.

In another aspect, the processor is further configured to activate an alarm of the electronic device in response to a generated fall classification, and in response to receiving a button input of the electronic device within a first threshold period of time from alarm activation, refrain from transmitting the notification that the wearer of the electronic device has fallen. The notification is transmitted if a button input is not received within a second threshold period of time from alarm activation that is longer than the first threshold period of time.

In another aspect, the apparatus further includes a heart rate sensor. The processor is further configured to determine a heart rate of the wearer of the electronic device, by: sampling heart-rate signal data from the heart rate sensor at a first frequency; determining signal points of decreased measurements in the heart-rate signal data; calculating an average distance between the signals points of decreased measurements; and calculating a current heart rate of the wearer of the electronic device as a ratio of the first frequency of the heart rate sensor to the calculated average distance.

In another aspect, the processor is further configured to determine an abnormal heart rate of the wearer of the apparatus based on a comparison of the calculated heart rate to a stored previously-measured heart rate, and transmit, via the wireless communication component of the electronic device, a notification of an abnormal heart beat.

In another aspect, the wireless communications component includes a cellular data transceiver and a Bluetooth Low Energy data transceiver.

In another aspect, the wireless communications component is configured to transmit the notification to a second party associated with the wearer of electronic device.

According to one aspect, a computer-implemented method for fall detection of a wearer of an electronic device is provided. The method includes sampling signal data received from an accelerometer of the electronic device, and responsive to determining that a first portion of the signal data exceeds a first threshold indicative of a fall of a wearer of the electronic device and that a second portion of the signal data is within a range indicative of motion stillness following the fall, generating a preliminary indication of fall detection associated with the signal data. The method further includes applying a machine learning classifier to the signal data associated with the preliminary indication to generate a fall classification indicating the signal data represents a fall of the wearer of the electronic device; and transmitting, via a wireless communication component of the electronic device, a notification that the wearer of the electronic device has fallen.

According to another exemplary aspect, a computer-readable medium is provided comprising instructions that comprises computer executable instructions for performing any of the methods disclosed herein.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplarily pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Exemplary aspects are described herein in the context of a system, method, and computer program product for fall detection of a wearer of an electronic device. Those of ordinary skill in the art will realize that the following description is illustrative only and is not intended to be in any way limiting. Other aspects will readily suggest themselves to those skilled in the art having the benefit of this disclosure. Reference will now be made in detail to implementations of the example aspects as illustrated in the accompanying drawings. The same reference indicators will be used to the extent possible throughout the drawings and the following description to refer to the same or like items.

Figure 1:
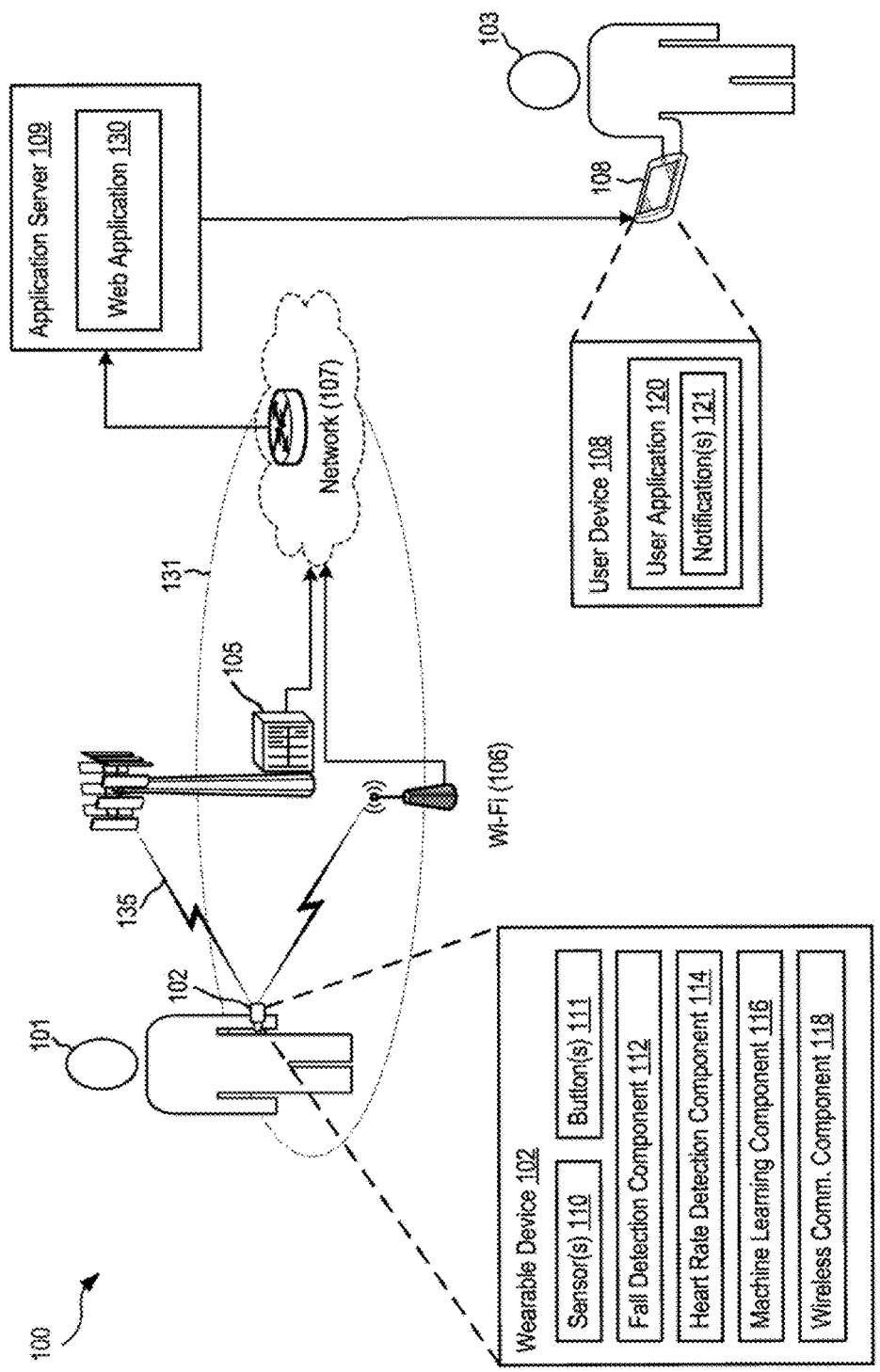
FIG. 1 is a block diagram illustrating a system for fall detection of a wearer of an electronic device according to an exemplary aspect.

FIG. 1 is a block diagram illustrating a system 100 for fall detection of a wearer 101 of an electronic device 102 according to an exemplary aspect. The system 100 includes a wearable device 102 configured to be equipped by a user (wearer 101) and to perform automated monitoring for fall detection, heart rate (HR), pulse, location, body temperature, inactivity, and other health-related issues. The wearable device 102 may be configured to transmit information directly to an application server 109, instead of a call-center, via a network 107 by way of a cellular base station 104 or a wireless access point 106. The application server 109 may be configured to relay to a user device 108 (as operated by a third party 103) executing a user application 120 one or more notifications 121 related to the activity of the wearer 101. In one particular example, the wearer 101 may be an elderly person, and the third-party user 103 may be a family member or caregiver of the wearer 101 seeking to receive real-time health information, location and possible fall notifications related to the wearer 101.

In one aspect, the wearable device 102 may include one or more sensors 110, one or more hardware input elements (e.g., buttons 111), a fall detection component 112, a heart rate detection component 114, a machine learning component 116, and a wireless communications component 118. In some aspects, the wearable device 102 may have a form factor configured to enable the wearable device to be worn on a wrist of the user, such as a bracelet or watch, although other configurations for wearing the device 102 may be utilized.

In an aspect, the one or more sensors 110 may be configured to obtain sensor signal data related to the health or activity of the wearer 101. Examples of the sensors 110 may include one or more accelerometers, gyroscopes, infrared sensors, heart rate sensors, light sensors, proximity sensors, touch sensors, compass, and a barometric altimeter. In some aspects, the wearable device 102 may include one or more input elements (buttons 111) configured to receive input, from the wearer 101, that confirms or cancels/overrides certain health alerts (such as a detected fall.) In some aspects, the wearable device 102 may include a limited number of hardware input elements (buttons 111), say, two or less, to simplify the user interface and improve the use experience for the wearer 101. The wearable device 102 may further include one or more output devices, including speakers for emitting an alarm, haptic-related devices for generating vibration, a graphical display (e.g., LED, LCD), In an aspect, the base station 105 may wirelessly communicate with the wearable device 102 via one or more base station antennas. The base station 105 (and other base stations, not shown) may provide communication coverage for a respective geographic coverage area 131. In some examples, the base station 105 may be referred to as a base transceiver station, a radio base station, an access point, an access node, a radio transceiver, a NodeB, eNodeB (eNB), gNB, Home NodeB, a Home eNodeB, a relay, or some other suitable terminology. Additionally, the plurality of base stations 105 may operate according to different ones of a plurality of communication technologies (e.g., 5G (New Radio), fourth generation (4G)/LTE, 3G, GSM, CDMA, Wi-Fi, Bluetooth, etc.), and thus there may be overlapping geographic coverage areas 131 for different communication technologies.

The wearable device 102 may be configured to establish one or more wireless communication links 135 with one or more base stations 105. The wireless communication links 135 shown in wireless communication network of the system 100 may carry uplink (UL) transmissions from the wearable device 102 to a base station 105, or downlink (DL) transmissions, from a base station 105 to the wearable device 102. The wireless communications network of the system 100 may further include a base station (access point 106) operating according to Wi-Fi technology, e.g., Wi-Fi access points, in communication with the wearable device 102 operating according to Wi-Fi technology, e.g., Wi-Fi stations (STAs) via communication links in an unlicensed frequency spectrum (e.g., 5 GHz) or via Bluetooth® Low Energy.

The application server 109 may include a web application 130 configured to coordinate with the wearable device 102 to facilitate performing automatic fall detection, heart rate measurement, and push notifications for detected falls and measured heart rates and may include several machine learning and artificial intelligence algorithms to improve the automated fall detection and eliminate false alarms.

Figure 2:
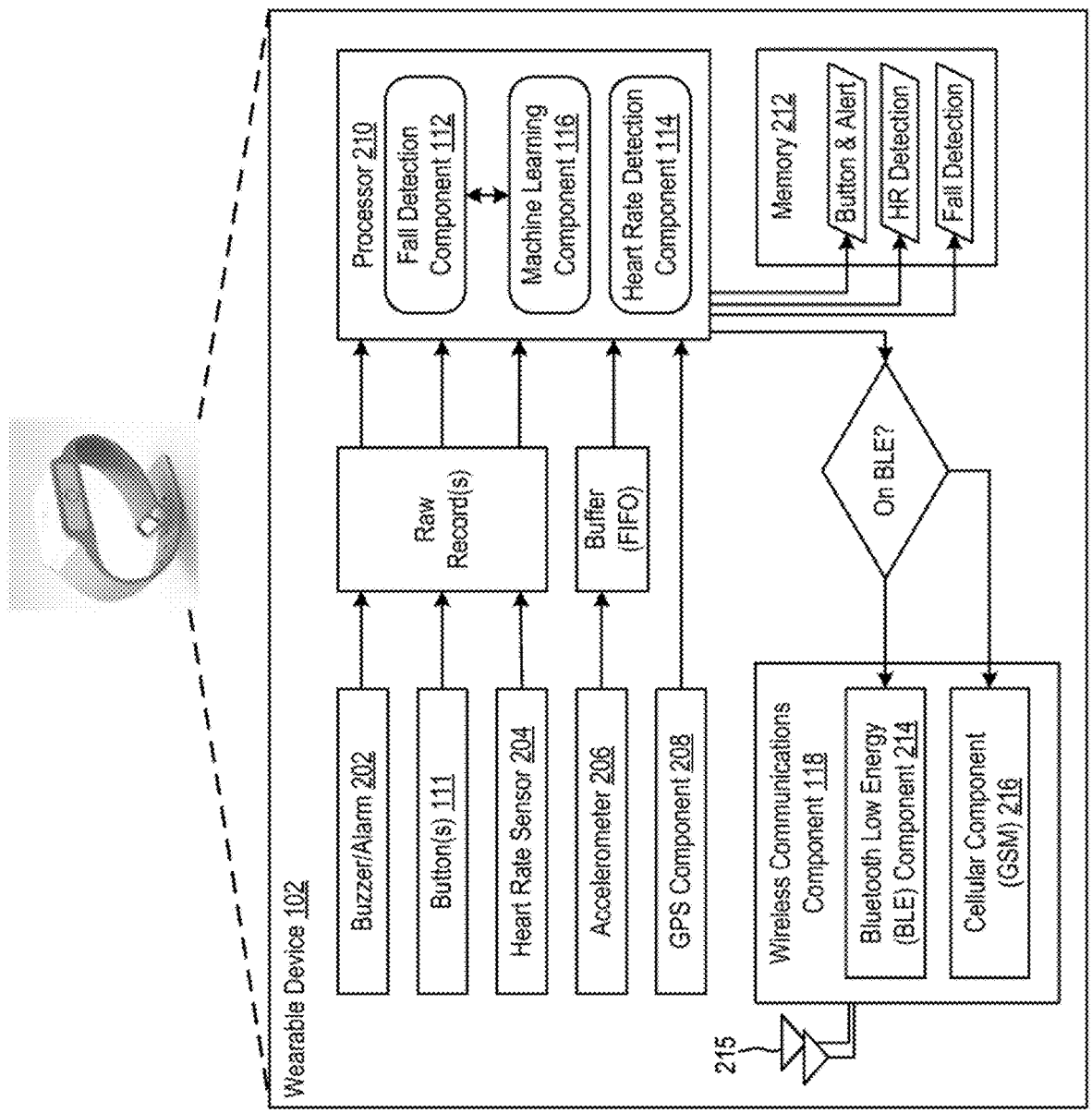
FIG. 2 is a block diagram illustrating the wearable device of FIG. 1 in greater detail according to an exemplary aspect.

FIG. 2 is a block diagram illustrating the wearable device 102 of FIG. 1 in greater detail according to an exemplary aspect. As shown, the wearable device 102 may include a buzzer or alarm component 202 configured to provide audio/visual feedback to the wearer when the wearable device requires user input or user intervention and provide reminders, for example for taking prescribed medicine. The wearable device 102 may include a heart rate sensor 204 configured to generate heart rate sensors data based one or more measurements related to the wearer 101. The wearable device 102 may include an accelerometer 206 configured to generate signal data related to the motion of the device 102 (and in turn, the wearer 101). The wearable device 102 may further include a global-positioning-system (GPS) component 208 configured to receive one or more location-based signals from one or more GPS transmitters that may be used to identify the geographical location of the wearable device 102.

In some aspects, the wearable device 102 may include a processor 210 and a memory 212 configured to receive signal data and other input data from any of the buzzer/alarm 202, button(s) 111, heart rate sensor 204, accelerometer 206, and GPS component 208. The processor 210 may include the sub-components a machine learning component 116, a fall detection component 112, and a heart rate detection component 114. The memory 212 may be any memory or storage device, which may store generated output from the processor, including indications of button presses, alert statuses, indications of abnormal heart rate detection, and indications of a fall detection. As shown, the processor 210 may be communicatively connected to the wireless communications component 118.

In one aspect, the wireless communications component 118 may include a sub-component 214 configured to perform short-range wireless communications using one or more antennas 215, such as according to the Bluetooth Low Energy (BLE) protocol. For example, the BLE component 214 may transmit and receive communications with the application server 109 via an access point 106 using a combination of BLE and Wi-Fi communication protocols. The wireless communications component 118 may further include a sub-component 216 configured to perform wireless cellular communications using one or more antennas 215, such as according to the GSM (or CDMA or TDMA) cellular communications protocol. In some aspects, the processor 210 may selectively operate the wireless communications component 118 to switch between communication modes (i.e., BLE or GSM) according to availability of base stations, access points, interference, and other network conditions. In one aspect, the wireless communications component 118 may be a low-power, system-on-chip (SoC) for Bluetooth low energy applications, and includes an RF transceiver, microcontroller, in-system programmable flash memory, and other integrated sub-components.

Fall Detection

According to an aspect, the fall detection component 112 may be configured to perform fall detection of the wearer 101 of the device 102 using a two-step approach: first, a preliminary pattern recognition algorithm to determine whether the system should execute the second step, and second, a machine learning algorithm for determining with high precision (few false positives) whether the signal represents a fall.

Listing 1, below, contains pseudocode configured to perform the pattern recognition on the sampled sensor data to generate an indication of a preliminary indication of fall detection ("POSSIBLE_FALL"). In one particular aspect, the fall detection component 112 may track three "channels" of the signal obtained from the accelerometer 206 and that refer to parts of the signal that matches certain expectations. For sake of discussion, these channels are labeled "green", "yellow", and "red". As shown below, the red channel of sensor data may be associated with a high level of acceleration (e.g., that may be used to characterize an impact). The yellow channel may be associated with a medium level of acceleration. The green channel of sensor data may be associated with a low level of acceleration (e.g., that may be used to characterize a period of inactivity following the impact). In one implementation, signal data is collected from the accelerometer 206 at 100 Hz. It may be stored in a temporary buffer (e.g., in a FIFO manner). In one implementation, the pattern recognition run on sequences of 10 seconds, therefore resulting in 100 points of data (i.e., "acceleration points").

The below algorithm considers the magnitude of the acceleration (line 2), but other aspects of the present disclosure may be extended to further consider the direction of the acceleration.

Listing 1: Pseudo-code for Fall Detection

```
1   For each acceleration point {
2       float mag = sqrt(x*x + y*y + z*z); // magnitude
3       if (mag > RED_CH_THRESHOLD) {
4           red_channel_expiration = RED_CH_MAX_AGE;
5           green_channel_cnt = green_channel_tolerance_cnt = 0;
6       }
7       else if (red_channel_expiration == 0) {
8           green_channel_cnt = green_channel_tolerance_cnt = 0;
9       }
10      else {
11          red_channel_expiration--;
12          if ((mag >= GREEN_CH_MIN) && (mag <= GREEN_CH_MAX)) {
13              green_channel_cnt++;
14          }
```

Listing 1: Pseudo-code for Fall Detection

```
15      else if ((green_channel_cnt > GREEN_CH_TOLERANCE_SKIP) &&
    (green_channel_tolerance_cnt < GREEN_CH_TOLERANCE)) {
16         green_channel_cnt++;
17         green_channel_tolerance_cnt++;
18      }
19      else {
20         green_channel_cnt = green_channel_tolerance_cnt = 0;
21      }
22    }
23  }
24
25  if (green_channel_cnt >= GREEN_CH_MIN_LEN)
26     return POSSIBLE_FALL;
27  else
28     return NOT_FALL;
```

In one aspect, the fall detection component 112 may sample signal data received from the accelerometer 206, and perform a preliminary pattern recognition on the sampled signal data. The fall detection component 112 may be configured to detect a pattern of a fall characterized by an impact (i.e., high acceleration) followed by some motion stillness (i.e., very low acceleration). In some aspects, the fall detection component 112 may determine whether the signal data can be characterized by an impact (high acceleration from the red channel) followed by a period of very low acceleration (from the green channel). In some aspects, the fall detection component 112 may determine whether a first portion of the signal data exceeds a first threshold indicative of a fall of a wearer of the electronic device (line 3, RED_CH_THRESHOLD), and whether a second portion of the signal data is within a range indicative of motion stillness following the fall (line 12).

The above algorithm employs a number of tunable parameters, including a parameter indicating a minimum length of the green channel signal data (GREEN_CH_MIN_LEN), a parameter indicating a tolerance value for the green channel signal data, (GREEN_CH_TOLERANCE), a parameter indicting a tolerance value for skipping red channel signal data when characterizing the green channel signal data (GREEN_CH_TOLERANCE_SKIP), a parameter for first threshold value for red channel signal data indicating a fall or impact (RED_CH_THRESHOLD), a parameter for a maximum age of the red channel signal data (RED_CH_MAX_AGE), and a parameter for threshold values of green channel signal data defining a range of values associated with the motion inactivity (GREEN_CH_MIN and GREEN_CH_MAX). It has been determined that modifying these parameters can increase or decrease the sensitivity of the pattern recognition algorithm, in particular the parameters associated with the red channel of signal data.

In some aspects, the fall detection component 112 may detect a fall at least in part based on a red channel age parameter (RED_CH_MAX_AGE) that regulates how long the system waits for a pattern of low acceleration (green channel) after high acceleration (red channel) is triggered. If the red channel signal data ages out, the fall detection component ignores a subsequent green pattern. This may be used to handle the case in which (acceleration-based) inactivity occurs too late after an impact. For example, the fall detection component 112 may detect an impact at time 9:00 and a period of inactivity at time 10:30, but would determine this is not a case of a fall and rule it out.

In some aspects, the fall detection component 112 may detect a fall at least in part based on a green-channel tolerance skip parameter (GREEN_CH_TOLERANCE_SKIP) that configures how many signal points can be ignored between red and green channels, while still detecting the pattern of an impact followed by inactivity. This may be used to handle the case that after an impact, a wearer of the electronic device might have some other movements before becoming unresponsive, such as rolling, bouncing, or spasms. In another aspect, the fall detection component 112 may detect a fall at least in part based on a green channel tolerance parameter (GREEN_CH_TOLERANCE) that configures how many signal points can be ignored in the green channel, in general. It has been determined that, in practice, the green channel of signal data may be highly sensitive, and the accelerometer readings can be noisy and imperfect. The fall detection component 112 may use the green-channel tolerance parameter to ignore or allow a certain number of readings to be out of range while still characterizing signal data as green channel. Nevertheless, in response to calculating a count of out-of-interval readings exceeds the green channel tolerance parameter, the fall detection component 112 may refrain from characterizing a portion of the signal data as green channel.

In some aspects, the fall detection component 112 may incorporate signal data from other sensors 110 of the electronic device in its determination of whether a fall has occurred. For example, the fall detection component 112 may determine if a fall of the wearable device has occurred based on, in addition to accelerometer signals, an abnormal heart rate measurement representing that the wearer of the wearable device 102 may be in physiological distress. In some aspects, the fall detection component 112 may refrain from detecting a fall in response to an indication from a proximity sensor of the wearable device that the user is not currently wearing the wearable device (e.g., if the unworn device has simply fallen off a table, if the device has fallen off the user themselves). In some aspects, the fall detection component may refrain from detecting a fall in response to an indication from the heart rate sensor 204 that the user is not wearing the device (e.g., a null heart rate measurement).

In one aspect, in response to a preliminary determination of a fall, the fall detection component 112 may then apply a machine learning classifier (e.g., machine learning component 116) to the signal data to generate a fall classification indicating the signal data represents a fall of the wearer of the electronic device. In some aspects, the machine learning component 116 may be configured as a shallow convolutional neural network architecture, training of network (weights), and implementation of an inference engine (framework) that will help eliminate false positive alarms (fall detected) and optimally execute all computations specified by the neural network architecture on the wearable device 102 embedded computational system. In an aspect, the neural network of the machine learning component 112 may be trained by an analysis of a large set of data, containing both accelerometer readings from persons falling, and from normal wear. The network may be trained via a feedback mechanism to properly label (i.e., classify) the fall data versus non-fall data.

If a fall is detected using the machine learning component 116, the fall detection component 112 may transmit, via the wireless communications component 118, a notification 121 that the wearer 101 of the electronic device has fallen. In some aspects, the fall detection component 112 may generate a notification 121 that includes other well-being or biometric information measured from other sensors 110 or other sub-components of the wearable device 102. For example, the fall detection component 112 may query the heart rate detection component 114 for a heart rate measurement to be included with the fall notification to increase the context for the recipient of the fall notification, e.g., know if the wearer is in further physical distress. In another example, the fall detection component 112 may query for several heart rate measurements, e.g., from the time period prior to the detected fall, concurrent with the detected fall, and from the time period subsequent to the detected fall. In other aspects, the fall detection component 112 may query the GPS component 208 for the current geographic location of the wearable device 102 and include the geographic location into the fall notification 121. In this way, a recipient of the fall notification may be able to determine where the wearer of the wearable device 102 is if aid needs to be dispatched to their location.

In some aspects, the buttons 111 of the device 102 may be used to confirm or cancel notification of a detected fall. For example, the wearer 101 may cancel notification of an erroneous fall detection (e.g., if no fall took place), or cancel notification a detected fall that was minor (e.g., in which no help is desired). In some aspects, if the application server 109 detects an emergency, the application server 109 may instruct the wearable device 102 to ring the alarm 202. If the user presses the button 111 within a threshold period of time (e.g., 15 seconds), the wearable device 102 transmits a cancellation message to the application server 109, resulting in the application server 109 refraining from transmitting the notification 121. If the application server 109 does not receive an answer within another threshold period of time (e.g., 20 seconds) after the device 102 received the instructions, the application server 109 may send a notification message 121 to the application 120 (which may include text messages, etc.)

Figure 3:
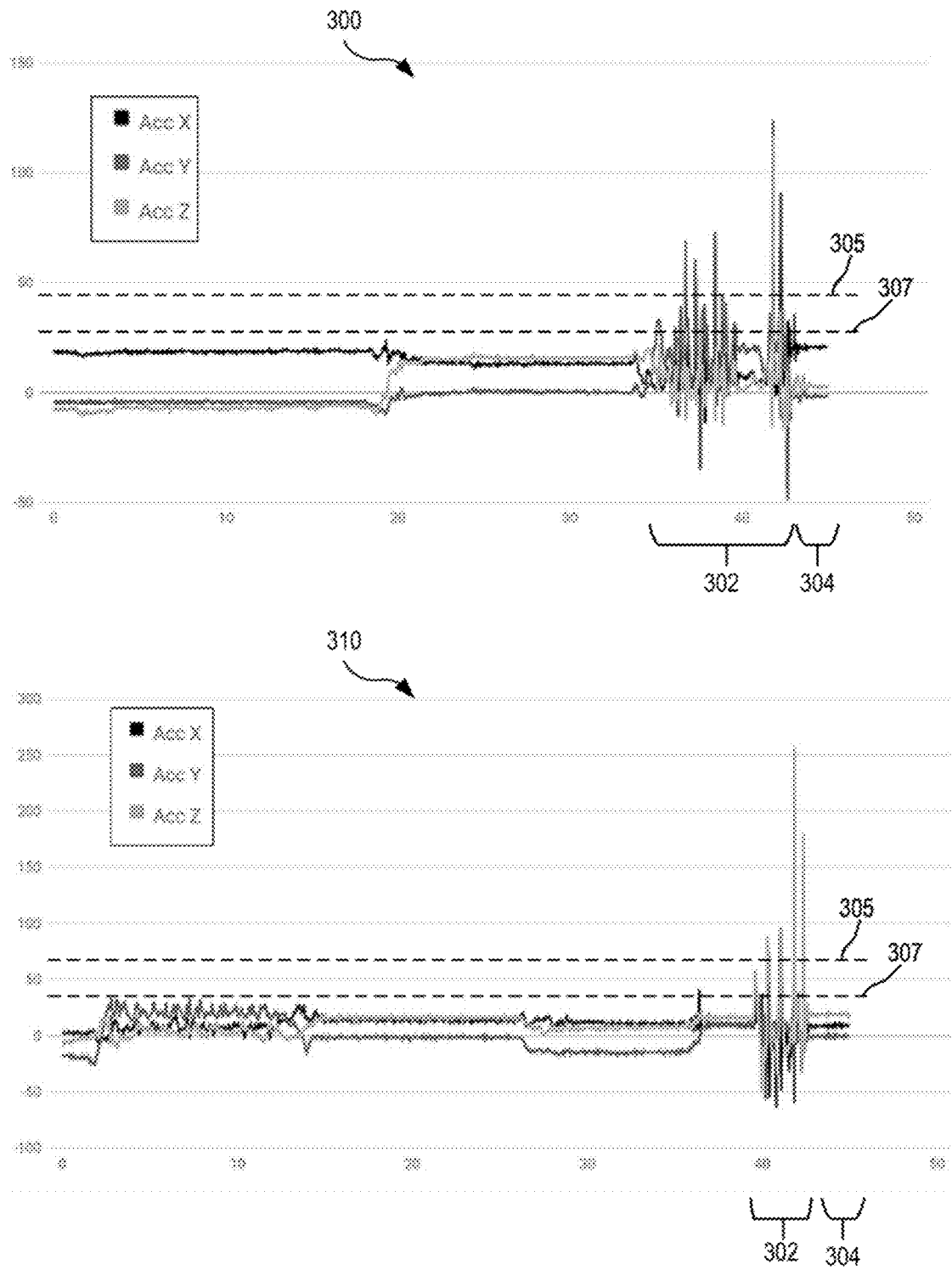
FIG. 3 is a chart illustrating a graph of signal data measured by the accelerometer and used for fall detection.

FIG. 3 is a chart illustrating graphs 300, 310 of signal data measured by the accelerometer and used for fall detection. Graph 300 includes multiple channels ("Acc X", "Acc Y", "Acc Z") of signal data received from the accelerometer 206 received over a period of time (e.g., t=0 to t=50). As described earlier, the fall detection component 112 detects the accelerometer signal data exceeds a threshold (shown as dashed line 305) representing an impact in a first portion of the signal data (e.g., at least one of the channels Acc X, during a first period of time 302). The fall detection component 112 may further determine the accelerometer signal data is within a range (demarcated by a dashed line 307) representing motion stillness following a possible fall, in a second portion of the signal data during a subsequent period of time 304, in a same (e.g., "Acc X") or different (e.g., "Acc Y") channel of signal data. Also shown in FIG. 3, graph 310 depicts another exemplary accelerometer signal data having a first portion 302 of signal data and a second portion 304 of signal data that are characteristic of a fall of a wearer of the user device.

Heart Rate Detection

According to an aspect, the heart rate detection component 114 may be configured to determine a heart rate of the wearer of the device 102 using a pattern recognition approach. The heart rate detection component 114 may sample heart-rate signal data from the heart rate sensor 204 of the electronic device, and look for points of large decreases in the heart rate signal, and averages the distance between the points. For sake of discussion, the distances' unit of measure is referred to herein as "signal points." In some aspects, the signal data received from the heart rate sensor 204 may represent a level of light intensity detected by the heart rate sensor 204.

Listing 2 below provides pseudocode configured to perform the pattern recognition on the sampled heart rate sensor data to calculate a heart rate of the user.

Listing 2: Pseudo-code for Heart Rate Detection

1. Remove the outliers in the signal data
2. Find points where heart rate signal shows significant decreases
3. Distances[ ] = array of the distance between the points found above
4. Avg_distance = average(Distances)
5. If StdDev(Distances) = 0
    Confidence = 1
6. else
    Confidence = min(1, ConstantFactor/StdDev(Distances))
7. Heart_rate = 60 * frequency/avg_distance
8. Return [Heart_rate and Confidence]

In some aspects, the heart rate detection component 114 may determine signal points of decreased measurements in the heart-rate signal data (line 2). The heart rate detection component 114 may then calculate an average distance between the signals points of decreased measurements (line 4), and calculate a current heart rate of the wearer of the device 102 as a ratio of the frequency of the heart rate sensor to the calculated average distance (7). For example, the heart rate sensor frequency may be 50 Hz, resulting in 50 signals per second. As such, the average beats-per-second is calculated as 50/average distance. Therefore, the final calculated heart rate in beats-per-minute is computed as 60*50/average distance. In some aspects, the heart rate detection component 114 may further calculate a confidence level associated with the calculated heart rate (lines 5-6).

In some aspects, the heart rate detection component 114 may determine what constitutes a significant decrease (for purposes of identifying signal points) according to a predetermined value. In other aspects, the heart rate detection component may determine what constitutes a significant decrease based on an iterative calculation that incrementally calculates a threshold value based on a best-confidence criterion. An example iterative calculation is show in pseudocode in Listing 3 below. As shown, the algorithm initiates using a value X and iterates, on each iteration increasing the value of X (e.g., by 5%) until a value is reached that is impermissible high (e.g., 1000000). Then, the results are gathered and the value of X is chosen that has the best confidence.

Listing 3: Pseudo-code for Heart Rate Signal Processing

```
bestConfidence = -1
bestHR = -1
max = -1
for(i =100; i< 1000000; i *= 1.05) {
    (confidence, detectedHR) = runHRDetect(i)
    if (confidence > max) {
        bestConfidence = confidence
        bestHR = detectedHR
    }
}
```

In some aspects, the heart rate detection component 114 may be configured to store and track the calculated heart rates, for example, as time-series data. As such, the heart rate detection component 114 may determine an abnormal heart rate of the wearer 101 based on a comparison of a current calculated heart rate to a stored previously-measured heart rate. In some aspects, the heart rate detection component 114 may transmit, via the wireless communications component 118, a notification of an abnormal heart beat.

Figure 4:
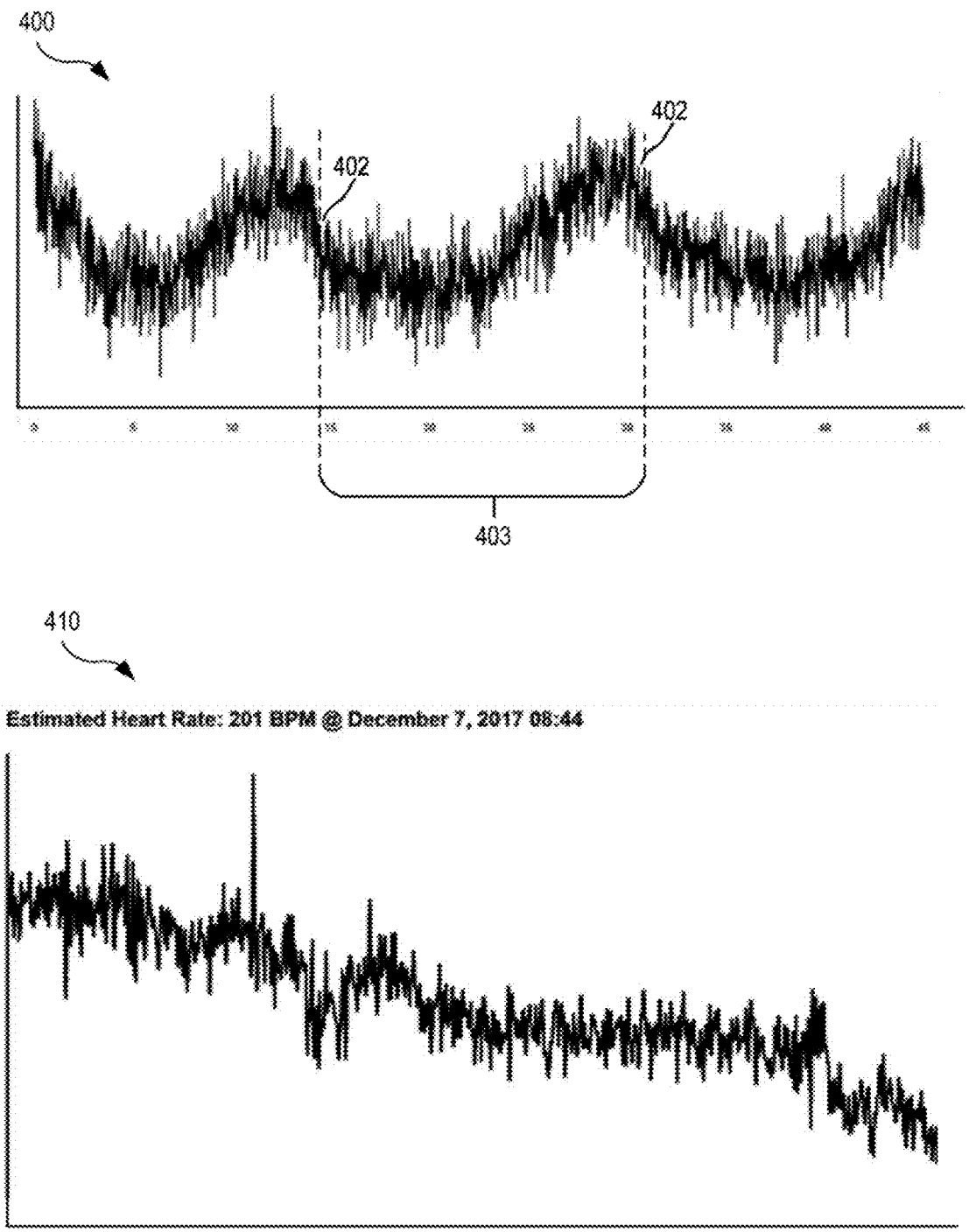
FIG. 4 is a chart illustrating a graph of signal data measured by a sensor and used for heart rate measurement.

FIG. 4 is a chart illustrating graphs 400, 410 of signal data measured by a sensor and used for heart rate measurement. As shown in graph 400, the signal data from the heart rate sensor may include signal points of decreased measurements in the heart-rate signal data (points 402), where an example distance between signal points is shown as distance 403. The heart rate detection component 114 may calculate a heart rate of the wearer of the device 102 as a ratio of the frequency of the heart rate sensor to an average distance. Graph 410 shown in FIG. 4 depicts another example signal data from a heart rate sensor 204 in which the measured heart rate may decline over a period of time.

Figure 5:
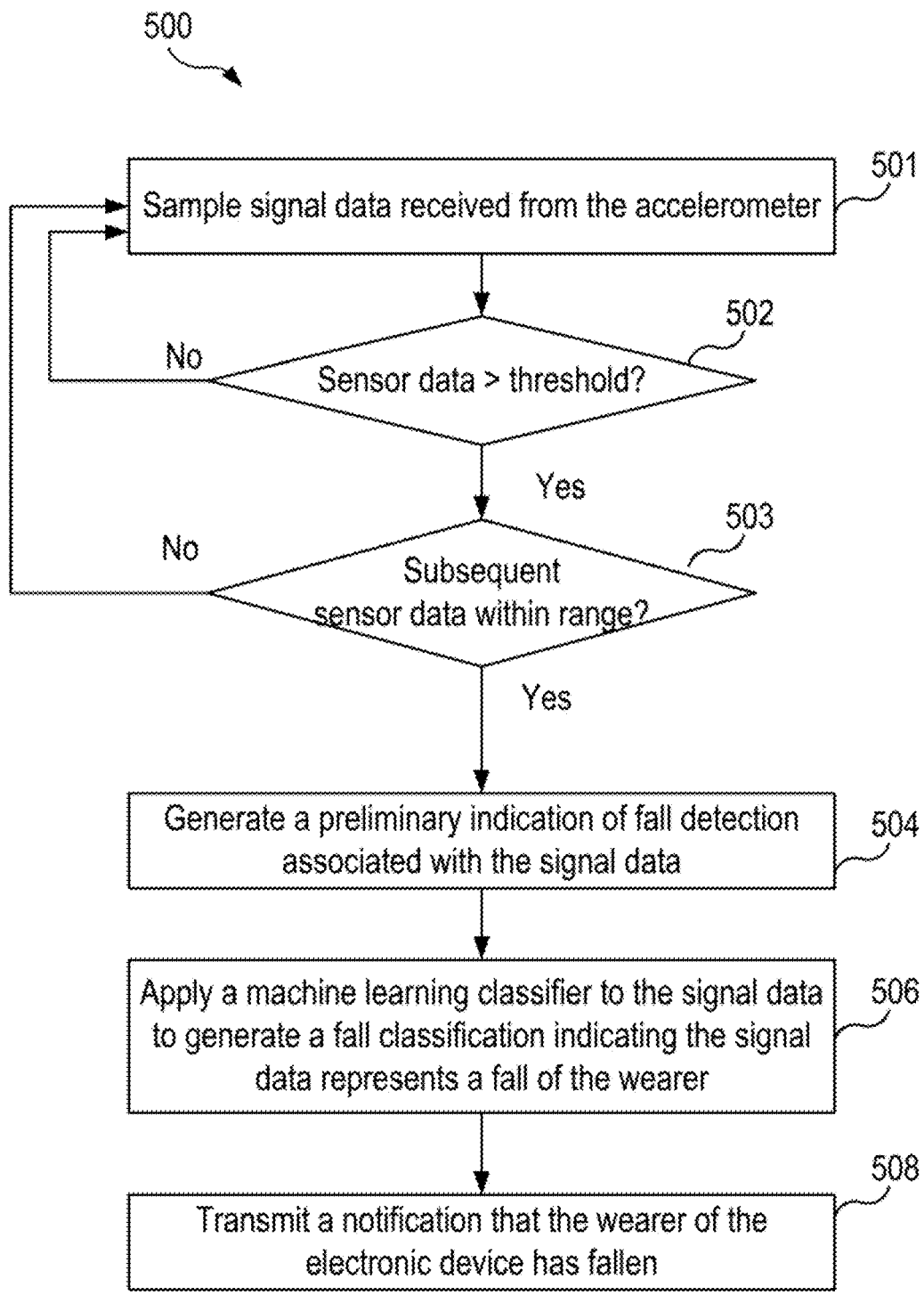
FIG. 5 is a flowchart illustrating a method for fall detection of a wearer of an electronic device, according to an exemplary aspect

FIG. 5 is a flowchart illustrating a method 500 for fall detection of a wearer of an electronic device, according to an exemplary aspect. It is noted that the following description of the exemplary method makes reference to the system and components described above.

The method 500 begins at 501, in which the fall detection component 112 samples signal data received from an accelerometer 206 of the electronic device (e.g., wearable device 102).

At steps 502 and 503, the fall detection component 112 determines whether a first portion of the signal data exceeds a first threshold indicative of a fall of a wearer of the electronic device and a second portion of the signal data is within a range indicative of motion stillness following the fall. 9. If so, at step 504, the fall detection component 112 generates a preliminary indication of fall detection associated with the signal data. Otherwise, the fall detection component 112 may return operations to step 501 and continue sampling accelerometer signal data.

In some aspects, the first portion of the signal data comprises a first channel of signal data from the accelerometer during a first time period, and the second portion of the signal data comprises a second channel of signal data from the accelerometer during a second time period subsequent to the first time period.

At step 506, the fall detection component 112 may apply a machine learning classifier to the signal data associated with the preliminary indication to generate a fall classification indicating the signal data represents a fall of the wearer of the electronic device.

At step 508, the fall detection component 112 may transmit, via a wireless communications component 118 of the electronic device, a notification that the wearer of the electronic device has fallen. In some aspects, the wireless communications component 118 comprises a cellular data transceiver and a Bluetooth Low Energy data transceiver. In some aspects, transmitting the notification comprises transmitting the notification to a second party associated with the wearer of electronic device.

In some aspects, the fall detection component 112 may activate an alarm of the electronic device in response to a generated fall classification. In response to receiving a button input of the electronic device within a first threshold period of time from alarm activation, the fall detection component 112 may refrain from transmitting the notification that the wearer of the electronic device has fallen. Otherwise, the notification may be transmitted if a button input is not received within a second threshold period of time from alarm activation that is longer than the first threshold period of time.

In another aspect, a heart rate detection component 114 of the wearable device may further determine a heart rate of the wearer of the electronic device, by: sampling heart-rate signal data from a heart rate sensor of the electronic device at a first frequency, determining signal points of decreased measurements in the heart-rate signal data, calculating an average distance between the signals points of decreased measurements, and calculating a current heart rate of the wearer of the electronic device as a ratio of the first frequency of the heart rate sensor to the calculated average distance. In some aspects, the heart rate detection component 114 may determine an abnormal heart rate of the wearer of the apparatus based on a comparison of the calculated heart rate to a stored previously-measured heart rate, and transmit, via the wireless communication component of the electronic device, a notification of an abnormal heart beat.

Figure 6:
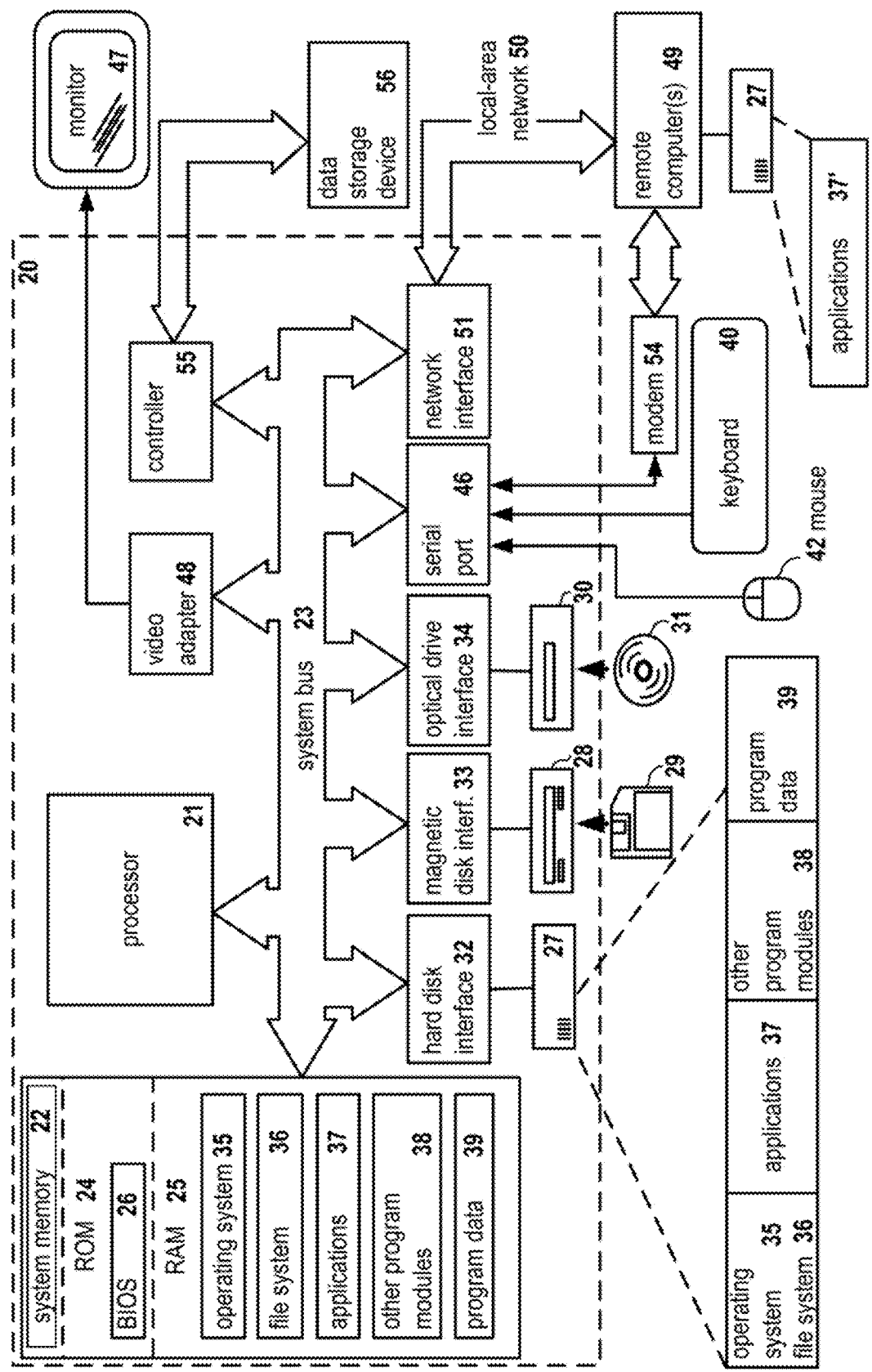
FIG. 6 is a block diagram of a special-purpose computer system on which the disclosed system and method can be implemented according to an exemplary aspect.

FIG. 6 is a block diagram illustrating a special-purpose computer system 20 on which aspects of systems and methods for fall detection of a wearer of an electronic device may be implemented in accordance with an exemplary aspect. It should be noted that the computer system 20 can correspond to the application server 109 or user device 108, for example, described earlier.

As shown, the computer system 20 (which may be a personal computer or a server) includes a central processing unit 21, a system memory 22, and a system bus 23 connecting the various system components, including the memory associated with the central processing unit 21. As will be appreciated by those of ordinary skill in the art, the system bus 23 may comprise a bus memory or bus memory controller, a peripheral bus, and a local bus that is able to interact with any other bus architecture. The system memory may include permanent memory (ROM) 24 and random-access memory (RAM) 25. The basic input/output system (BIOS) 26 may store the basic procedures for transfer of information between elements of the computer system 20, such as those at the time of loading the operating system with the use of the ROM 24.

The computer system 20, may also comprise a hard disk 27 for reading and writing data, a magnetic disk drive 28 for reading and writing on removable magnetic disks 29, and an optical drive 30 for reading and writing removable optical disks 31, such as CD-ROM, DVD-ROM and other optical media. The hard disk 27, the magnetic disk drive 28, and the optical drive 30 are connected to the system bus 23 across the hard disk interface 32, the magnetic disk interface 33 and the optical drive interface 34, respectively. The drives and the corresponding computer information media are powerindependent modules for storage of computer instructions, data structures, program modules and other data of the computer system 20.

An exemplary aspect comprises a system that uses a hard disk 27, a removable magnetic disk 29 and a removable optical disk 31 connected to the system bus 23 via the controller 55. It will be understood by those of ordinary skill in the art that any type of media 56 that is able to store data in a form readable by a computer (solid state drives, flash memory cards, digital disks, random-access memory (RAM) and so on) may also be utilized.

The computer system 20 has a file system 36, in which the operating system 35, may be stored, as well as additional program applications 37, other program modules 38, and program data 39. A user of the computer system 20 may enter commands and information using keyboard 40, mouse 42, or any other input device known to those of ordinary skill in the art, such as, but not limited to, a microphone, joystick, game controller, scanner, etc. Such input devices typically plug into the computer system 20 through a serial port 46, which in turn is connected to the system bus, but those of ordinary skill in the art will appreciate that input devices may be also be connected in other ways, such as, without limitation, via a parallel port, a game port, or a universal serial bus (USB). A monitor 47 or other type of display device may also be connected to the system bus 23 across an interface, such as a video adapter 48. In addition to the monitor 47, the personal computer may be equipped with other peripheral output devices (not shown), such as loudspeakers, a printer, etc.

Computer system 20 may operate in a network environment, using a network connection to one or more remote computers 49. The remote computer (or computers) 49 may be local computer workstations or servers comprising most or all of the aforementioned elements in describing the nature of a computer system 20. Other devices may also be present in the computer network, such as, but not limited to, routers, network stations, peer devices or other network nodes.

Network connections can form a local-area computer network (LAN) 50 and a wide-area computer network (WAN). Such networks are used in corporate computer networks and internal company networks, and they generally have access to the Internet. In LAN or WAN networks, the personal computer 20 is connected to the local-area network 50 across a network adapter or network interface 51. When networks are used, the computer system 20 may employ a modem 54 or other modules well known to those of ordinary skill in the art that enable communications with a wide-area computer network such as the Internet. The modem 54, which may be an internal or external device, may be connected to the system bus 23 by a serial port 46. It will be appreciated by those of ordinary skill in the art that said network connections are non-limiting examples of numerous well-understood ways of establishing a connection by one computer to another using communication modules.

In various aspects, the systems and methods described herein may be implemented in hardware, software, firmware, or any combination thereof. If implemented in software, the methods may be stored as one or more instructions or code on a non-transitory computer-readable medium. Computer-readable medium includes data storage. By way of example, and not limitation, such computer-readable medium can comprise RAM, ROM, EEPROM, CD-ROM, Flash memory or other types of electric, magnetic, or optical storage medium, or any other medium that can be used to carry or store desired program code in the form of instructions or data structures and that can be accessed by a processor of a general purpose computer.

In various aspects, the systems and methods described in the present disclosure can be addressed in terms of modules. The term "module" as used herein refers to a real-world device, component, or arrangement of components implemented using hardware, such as by an application specific integrated circuit (ASIC) or field-programmable gate array (FPGA), for example, or as a combination of hardware and software, such as by a microprocessor system and a set of instructions to implement the module's functionality, which (while being executed) transform the microprocessor system into a special-purpose device. A module may also be implemented as a combination of the two, with certain functions facilitated by hardware alone, and other functions facilitated by a combination of hardware and software. In certain implementations, at least a portion, and in some cases, all, of a module may be executed on the processor of a general purpose computer (such as the one described in greater detail in FIG. 6, above). Accordingly, each module may be realized in a variety of suitable configurations, and should not be limited to any particular implementation exemplified herein.

In the interest of clarity, not all of the routine features of the aspects are disclosed herein. It would be appreciated that in the development of any actual implementation of the present disclosure, numerous implementation-specific decisions must be made in order to achieve the developer's specific goals, and these specific goals will vary for different implementations and different developers. It is understood that such a development effort might be complex and time-consuming, but would nevertheless be a routine undertaking of engineering for those of ordinary skill in the art, having the benefit of this disclosure.

Furthermore, it is to be understood that the phraseology or terminology used herein is for the purpose of description and not of restriction, such that the terminology or phraseology of the present specification is to be interpreted by the skilled in the art in light of the teachings and guidance presented herein, in combination with the knowledge of the skilled in the relevant art(s). Moreover, it is not intended for any term in the specification or claims to be ascribed an uncommon or special meaning unless explicitly set forth as such.

The various aspects disclosed herein encompass present and future known equivalents to the known modules referred to herein by way of illustration. Moreover, while aspects and applications have been shown and described, it would be apparent to those skilled in the art having the benefit of this disclosure that many more modifications than mentioned above are possible without departing from the inventive concepts disclosed herein.

What is claimed is:

1. An apparatus for detecting a fall of a wearer of the apparatus, comprising:
   at least one sensor comprising an accelerometer configured to measure motion of the apparatus;
   a processor configured to:
   sample signal data received from the accelerometer;
   determine that a first portion of the signal data exceeds a first threshold indicative of the fall of the wearer of the apparatus and that a second portion of the signal data is within a range indicative of motion stillness following the fall, wherein the processor is further configured to ignore, while still monitoring for a pattern of an impact followed by the motion stillness, solely signal points that are not associated with a falling motion, exclusively between the first portion of the signal data and the second portion of the signal data, based on a tolerance range;
generate, in response to the determination, a preliminary indication of fall detection associated with the signal data;
apply, subsequent to generating the preliminary indication, a machine learning classifier to the signal data associated with the preliminary indication to generate a fall classification that improves a confirmation accuracy that the signal data represents the fall of the wearer of the apparatus;
activate an alarm of the apparatus in response to the generated fall classification;
in response to receiving a button input of the apparatus within a threshold period of time from alarm activation, wherein the button input cancels the alarm:
refrain from transmitting a notification indicative of the fall to a second party associated with the wearer; and
train the machine learning classifier via feedback indicating that the signal data does not represent the fall of the wearer.

2. The apparatus of claim 1, wherein the first portion of the signal data comprises a first channel of signal data from the accelerometer during a first time period, and the second portion of the signal data comprises a second channel of signal data from the accelerometer during a second time period subsequent to the first time period.

3. The apparatus of claim 1, wherein the processor is further configured to generate the preliminary indication in response to determining that a time difference between when the first portion of the signal data ends and when the second portion of the signal data begins is less than a predetermined wait time.

4. The apparatus of claim 1, further comprising a heart rate sensor, and wherein the processor is further configured to:
determine a heart rate of the wearer of the apparatus, by:
sampling heart-rate signal data from the heart rate sensor at a first frequency, wherein the heart-rate signal data represents a level of light intensity per signal point;
determining signal points of decreased measurements in the heart-rate signal data;
calculating an average amount of signal points between the signals points of decreased measurements; and
determining the heart rate of the wearer of the apparatus as a ratio of the first frequency of the heart rate sensor to the average amount of signal points.

5. The apparatus of claim 4, wherein the processor is further configured to:
determine an abnormal heart rate of the wearer of the apparatus based on a comparison of the heart rate to a stored previously-measured heart rate; and
transmit to the second party associated with the wearer a notification of an abnormal heart rate.

6. The apparatus of claim 1, further comprising:
in response to not receiving the button input of the apparatus within the threshold period of time from the alarm activation, wherein the button input cancels the alarm, transmit to the second party associated with the wearer the notification that the wearer of the apparatus has fallen.

7. The apparatus of claim 1, further comprising a wireless communications component, wherein the wireless communications component comprises a cellular data transceiver and a Bluetooth Low Energy data transceiver.

8. A computer-implemented method for fall detection of a wearer of an electronic device, comprising:
sampling signal data received from an accelerometer of the electronic device;
determining that a first portion of the signal data exceeds a first threshold indicative of the fall of the wearer of the electronic device and that a second portion of the signal data is within a range indicative of motion stillness following the fall, wherein the determining further comprises ignoring, while still monitoring for a pattern of an impact followed by the motion stillness, solely signal points that are not associated with a falling motion, exclusively between the first portion of the signal data and the second portion of the signal data, based on a tolerance range;
generating, in response to the determination, a preliminary indication of fall detection associated with the signal data;
applying, subsequent to generating the preliminary indication, a machine learning classifier to the signal data associated with the preliminary indication to generate a fall classification that improves a confirmation accuracy that the signal data represents the fall of the wearer of the electronic device;
activating an alarm of the electronic device in response to the generated fall classification;
in response to receiving a button input of the electronic device within a threshold period of time from alarm activation, wherein the button input cancels the alarm:
refraining from transmitting a notification indicative of the fall to a second party associated with the wearer; and
training the machine learning classifier via feedback indicating that the signal data does not represent the fall of the wearer.

9. The computer-implemented method of claim 8, wherein the first portion of the signal data comprises a first channel of signal data from the accelerometer during a first time period, and the second portion of the signal data comprises a second channel of signal data from the accelerometer during a second time period subsequent to the first time period.

10. The computer-implemented method of claim 8, further comprising generating the preliminary indication in response to determining that a time difference between when the first portion of the signal data ends and when the second portion of the signal data begins is less than a predetermined wait time.

11. The computer-implemented method of claim 8, further comprising:
determining a heart rate of the wearer of the electronic device, by:
sampling heart-rate signal data from a heart rate sensor of the electronic device at a first frequency, wherein the heart-rate signal data represents a level of light intensity per signal point;
determining signal points of decreased measurements in the heart-rate signal data;
calculating an average amount of signal points between the signals points of decreased measurements; and
determining the heart rate of the wearer of the electronic device as a ratio of the first frequency of the heart rate sensor to the average amount of signal points.

12. The computer-implemented method of claim 11, further comprising:
determining an abnormal heart rate of the wearer of the electronic device based on a comparison of the heart rate to a stored previously-measured heart rate; and
transmitting to the second party associated with the wearer a notification of an abnormal heart beat.

13. The computer-implemented method of claim 8, further comprising:
in response to not receiving the button input of the electronic device within the threshold period of time from the alarm activation, wherein the button input cancels the alarm, transmitting to the second party associated with the wearer the notification that the wearer of the electronic device has fallen.

14. The computer-implemented method of claim 8, wherein a wireless communications component of the electronic device comprises a cellular data transceiver and a Bluetooth Low Energy data transceiver.

15. A non-transitory computer readable medium comprising computer executable instructions for fall detection of a wearer of an electronic device, the instructions causing the electronic device to perform steps comprising:
sampling signal data received from an accelerometer of the electronic device;
determining that a first portion of the signal data exceeds a first threshold indicative of the fall of the wearer of the electronic device and that a second portion of the signal data is within a range indicative of motion stillness following the fall, wherein the determining further comprises ignoring, while still monitoring for a pattern of an impact followed by the motion stillness, solely signal points that are not associated with a falling motion, exclusively between the first portion of the signal data and the second portion of the signal data, based on a tolerance range;
generating, in response to the determination, a preliminary indication of fall detection associated with the signal data;
applying, subsequent to generating the preliminary indication, a machine learning classifier to the signal data associated with the preliminary indication to generate a fall classification that improves a confirmation accuracy that the signal data represents the fall of the wearer of the electronic device;
activating an alarm of the electronic device in response to the generated fall classification;
in response to receiving a button input of the electronic device within a threshold period of time from alarm activation, wherein the button input cancels the alarm:
refraining from transmitting a notification indicative of the fall to a second party associated with the wearer; and
training the machine learning classifier via feedback indicating that the signal data does not represent the fall of the wearer.

16. The non-transitory computer readable medium of claim 15, wherein the first portion of the signal data comprises a first channel of signal data from the accelerometer during a first time period, and the second portion of the signal data comprises a second channel of signal data from the accelerometer during a second time period subsequent to the first time period.

17. The non-transitory computer readable medium of claim 15, the instructions further causing the electronic device to perform steps comprising generating the preliminary indication in response to determining that a time difference between when the first portion of the signal data ends and when the second portion of the signal data begins is less than a predetermined wait time.

18. The non-transitory computer readable medium of claim 15, the instructions further causing the electronic device to perform steps comprising:
determining a heart rate of the wearer of the electronic device, by:
sampling heart-rate signal data from a heart rate sensor of the electronic device at a first frequency, wherein the heart-rate signal data represents a level of light intensity per signal point;
determining signal points of decreased measurements in the heart-rate signal data;
calculating an average amount of signal points between the signals points of decreased measurements; and
determining the heart rate of the wearer of the electronic device as a ratio of the first frequency of the heart rate sensor to the average amount of signal points.

* * * * *